US00PP10134P

United States Patent [19]

Van Vloten

[11] Patent Number: Plant 10,134

[45] Date of Patent: Dec. 2, 1997

[54] *JUNIPERUS HORIZONTALIS* NAMED 'BLUE PRINCE'

[75] Inventor: Casey Van Vloten, Abottsford, Canada

[73] Assignee: Bailey Nurseries, Inc., St. Paul, Minn.

[21] Appl. No.: 655,950

[22] Filed: May 31, 1996

[51] Int. Cl.[6] ..... A01H 5/00

[52] U.S. Cl. ..... Plt./50.2

[58] Field of Search ..... Plt./50.2

[56] References Cited

U.S. PATENT DOCUMENTS

P.P. 2,752 7/1967 Lee ..... Plt./50.2
P.P. 2,773 10/1967 Lee ..... Plt./50.2
P.P. 9,639 9/1996 Bergman ..... Plt./50.2

*Primary Examiner*—James R. Feyrer
*Attorney, Agent, or Firm*—Burns, Doane, Swecker & Mathis, L.L.P.

[57] ABSTRACT

A new and distinct variety of creeping juniper, *Juniperus horizontalis*, was discovered while growing in a seedbed of native plants of the same species. The new variety exhibits attractive intense steel blue fine-needled foliage combined with a low-growing extremely prostrate compact growth habit. The blue foliage coloration is substantially retained throughout the year with only a minimal fading in intensity during the winter. Good winter hardiness and resistance to diseases have been observed to date. Accordingly, the new variety can be considered to exhibit what appears to be juvenile foliage throughout the year. The new variety propagates well from cuttings and is particularly well suited for growing as a distinctive ground cover in a mass planting.

3 Drawing Sheets

SUMMARY OF THE INVENTION

The present invention relates to a new and distinct variety of creeping juniper, *Juniperus horizontalis*, that has been named 'Blue Prince'.

The new variety of the present invention was selected during 1985 or 1986 from among plants growing in a seedbed of *Juniperus horizontalis* that had been planted during 1983 at High River, Alberta, Canada. The seed used to plant such seedbed was collected from native seedlings of the same species growing in southern Alberta Canada. The original plant of the new variety subsequently was transplanted to Pitt Meadows, British Columbia, Canada, wher further observation and testing were carried out. I was primarily attracted to the new variety because of its atypical growth habit combined with the attractive deep steel blue coloration of the foliage. The exact parentage of the new variety is unknown, and its distinctiveness is of unknown causation.

It was found that the new variety of *Juniperus horizontalis:*

(a) exhibits attractive intense steel blue fine-needled foliage,
(b) exhibits an extremely prostrate compact growth habit, and
(c) is particularly well suited for growing as a ground cover.

The foliage of the new variety of the present invention does not assume a purplish coloration during the winter, but merely tends to lose some of the blue intensity and assumes a duller blue coloration during colder weather. The new foliage growth tends to be slightly lighter in coloration than the more mature foliage (as illustrated). Accordingly, the new variety can be considered to exhibit what appears to be juvenile foliage throughout the year. No disease problem has been observed during testing to date. For instance, no Juniper tip blight has been experienced. Excellent winter hardiness of the new variety has been confirmed while growing at Pitt Meadows, British Columbia, Canada.

The new variety, because of its intense steel blue foliage coloration combined with its prostrate growth habit, can be grown to particular advantage as an attractive ornamental ground cover in the form of a mass planting. It lends itself well to conventional container production methods and cultural practices, and well meets the demands of the modern landscape. Dense low-growing compact finely-textured plants are provided that require little maintenance while imparting distinctive coloration to the landscape throughout the year.

The new variety of the present invention is similar in growth habit and general appearance to that of the 'Prince of Wales' variety (non-patented in the United States) with the exception that the foliage is of an intense steel blue coloration (as illustrated) rather than green.

When compared to the 'Blue Chip' variety (non-patented in the United States), the new variety is found to (a) exhibit a lower growing, more prostrate, less upright and less mounding growth habit, (b) exhibit a slightly darker and more intense blue foliage coloation, and (c) exhibit a lesser tendency to display an open middle in the foliage of older plants. The breadth of the new variety at a given age generally is comparable to that of the 'Blue Chip' variety when plants of the same age are compared under comparable growing environments. Also, the 'Blue Chip' variety tends to exhibit smaller leaves.

When compared to the 'Bar Harbor' variety (non-patented in the United States), the branches of 'Bar Harbor' tend to be prostrate while those of the new variety are ascending. Also, 'Bar Harbor' tends to exhibit a lax branching character and longer internodes than the new variety which is more compact and more tightly branched.

When compared to the 'Hughes' variety (non-patented in the United States), the foliage of 'Hughes' tends to be greener in coloration.

When compared to the 'Wiltonii' variety (non-patented in the United States), 'Wiltonii' tends to form smaller leaves, a prostrate growth habit, and to form weaker growth that commonly results in the substantial absence of branches at the central area of the plant.

Asexual propagation of the new variety has been successfully carried out for a number of years at Pitt Meadows, British Columbia, Canada. Rooted cuttings have repeatedly demonstrated that the characterisitcs of the new variety as discussed herein are firmly fixed and are retained through successive generations of asexual propagation.

BRIEF DESCRIPTION OF THE PHOTOGRAPHS

The accompanying photographs show as nearly true as it is reasonably possible to make the same in color illustrations of this character, typical specimens of the new variety. The plants depicted in the photographs were approximately 3 to 4 years of age and were being grown in 5-gallon containers at Pitt Meadows, British Columbia, Canada.

FIG. 1. illustrates for comparative purposes generally at the left plants of the new variety and generally at the right plants of the 'Blue Chip' variety of *Juniperus horizontalis*. The considerably more prostrate and less upright growth habit and outwardly extending streamers of the new variety are apparent. The intense blue foliage coloration typically exhibited by the new variety is more accurately depicted in FIGS. 2 and 3 than in FIG. 1. The photograph of FIG. 1 was obtained during June, 1995.

DETAILED DESCRIPTION

Figure 1:
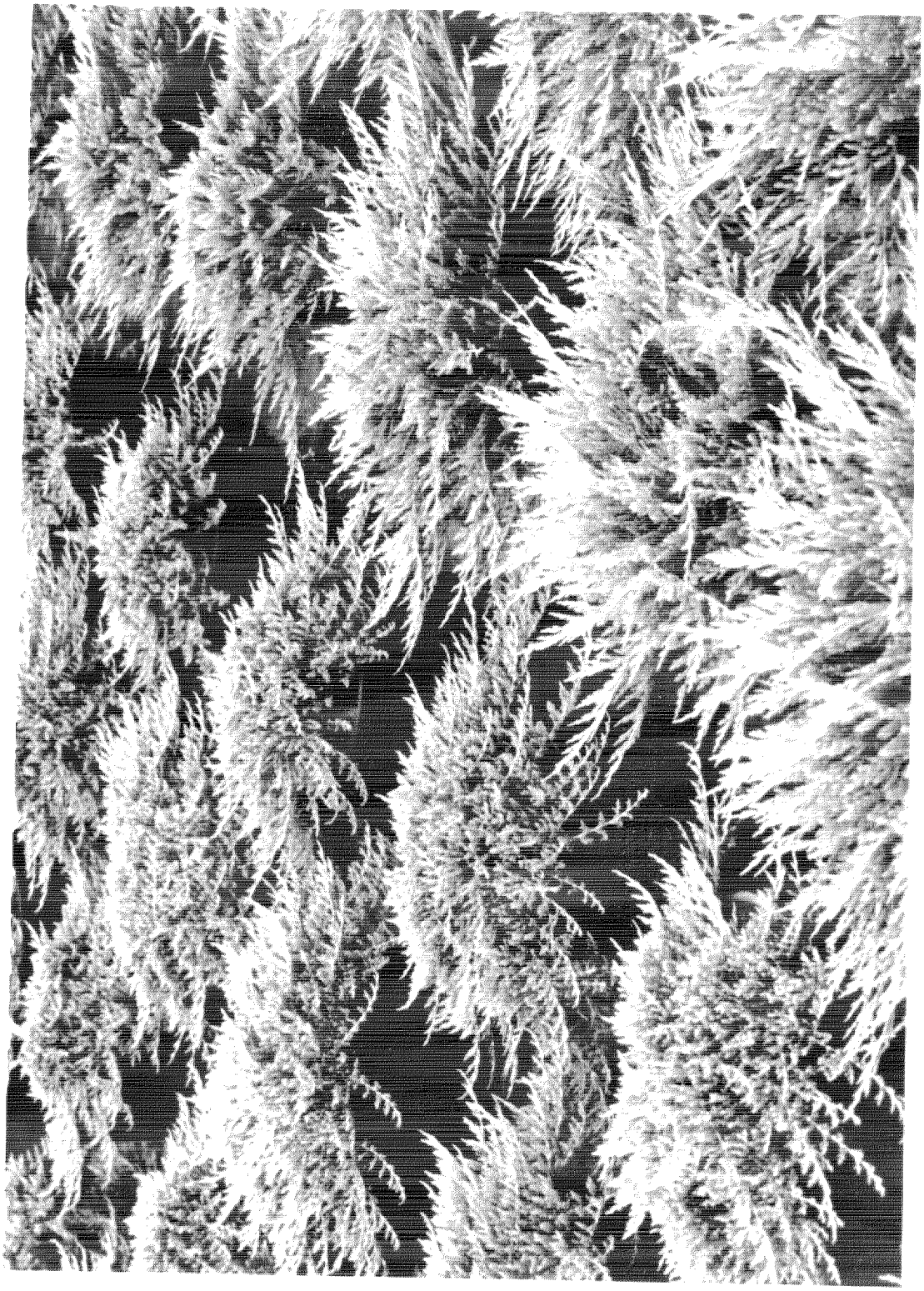
Figure 2:
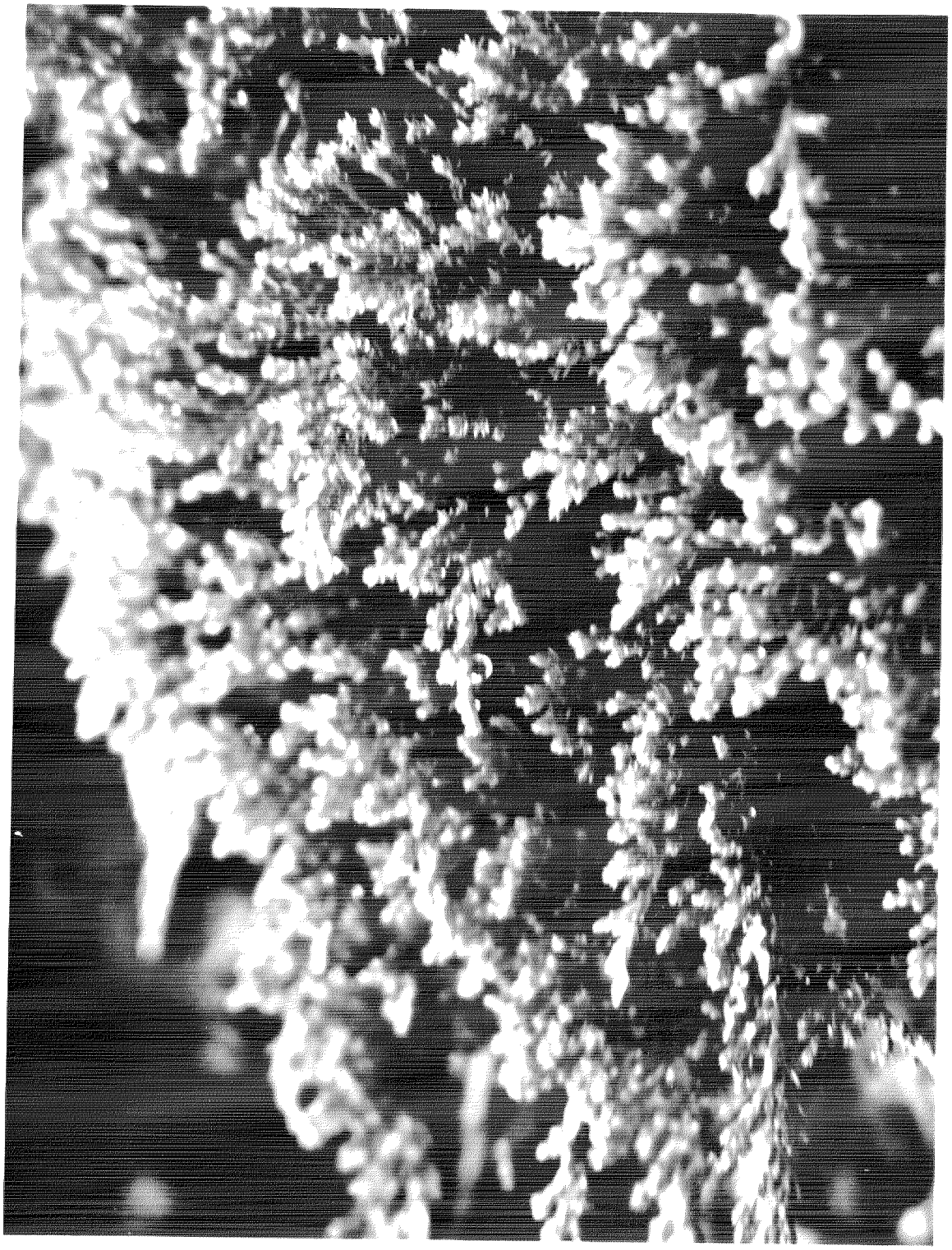
FIG. 2 illustrates a closer view of the intense steel blue foliage of the new variety. The photograph of FIG. 2 was obtained during August, 1993.
Figure 3:
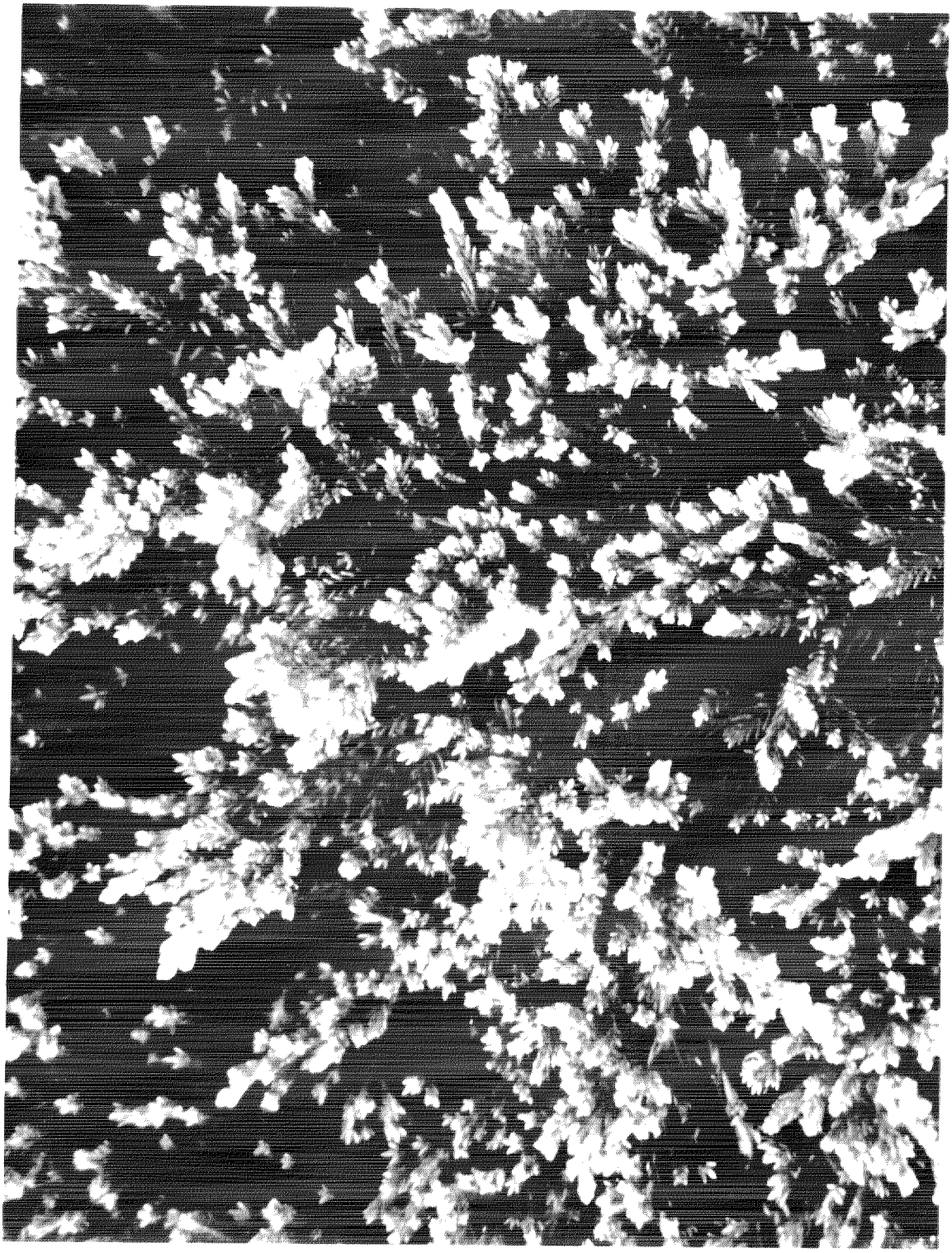
FIG. 3 illustrates a further closer view of the intense steel blue foliage of the new variety wherein even greater detail is visible. The photograph of FIG. 3 was obtained during August, 1993.

The chart used in the identification of color is the R.H.S. Colour Chart of The Royal Horticultural Society, London England. The plants described were grown in full sun at Pitt Meadows, British Columbia, Canada.

Classification: *Juniperus horizontalis*, 'Blue Prince' variety.

Foliage:

*Type.*—Finely textured (as illustrated).

*Color.*—Growing tips measuring approximately 2 mm. commonly tend to exhibit a brown appearance. During summer the mature foliage is intense steel blue, Blue-Green Group 122B, in coloration. The new growth tends to be slightly lighter in coloration. During the winter some of the intensity of the blue coloration tends to be lost and approaches Greyed-Green Group 189C; however, no purplish coloration is exhibited and the overall coloration of the foliage generally is well retained with only minor variation when colder weather is encountered. What appears to be juvenile foliage is exhibited throughout the year. When container grown, no scale leaves have been observed to date. The leaves are arranged as opposite decussate pairs that give the branch a symmetrical four-angled or four-ranked shape. Typical leaf lengths are approximately 6 mm., typical branch intervals are approximately 1 cm., and typical stem widths are approximately 3 to 4 mm. on the current year's growth. The branch orientation typically is ascending. A waxy bloom of medium intensity commonly is present that tends to be a paler yellow-green coloration on the underside of the branches and on the older foliage. Such bloom tends to be easily removed by rubbing.

Plant:

*Growth habit.*—Extremely prostrate and compact (as illustrated). Resists the formation of an open middle in mature plants to a greater degree than the 'Blue Chip' variety.

*Dimensions.*—A three- to four-year-old container-grown plant commonly exhibits a spread of approximately 18 to 24 inches, and a height of only approximately 2 to 4 inches. This compares to the more mounding growth habit and a height of approximately 5 to 6 inches, or more, for the 'Blue Chip' variety. The spread is generally comparable to that of the 'Blue Chip'. With age, plants of the new variety tend to spread while substantially retaining their initial height.

*Fertility.*—No berries have been observed to date.

*Propagation.*—It is preferred to take cuttings at any time after a frost in the Fall and the hardening of the foliage. These can then be finished indoors for 6 to 8 weeks under mist while providing conventional temperature conditions commonly used for the rooting of cuttings.

*Planting pattern.*—When forming a mass planting, a plant spacing of 30 to 36 inches is recommended.

*Disease resistance.*—No disease problem has been observed during testing to date. For instance, no Juniper tip blight has been experienced. Also, no evidence of mite damage has been observed to date.

*Winter hardiness.*—Has withstood winters at Pitt Meadows, British Columbia, Canada, with no winter damage.

I claim:

1. A new and distinct variety of *Juniperus horizontalis* which:

(a) exhibits attractive intense steel blue fine-needled foliage,
(b) exhibits an extremely prostrate compact growth habit, and
(c) is particularly well suited for growing as a ground cover;

substantially as herein shown and described.

* * * * *